United States Patent
Ayala

(10) Patent No.: US 7,566,463 B2
(45) Date of Patent: Jul. 28, 2009

(54) ORAL REHYDRATION COMPOSITIONS

(75) Inventor: Nelson Ayala, Lynchburg, VA (US)

(73) Assignee: C. B. Fleet Company, Lynchburg, VA (US)

( * ) Notice: Subject to any disclaimer, the term of this patent is extended or adjusted under 35 U.S.C. 154(b) by 415 days.

(21) Appl. No.: 11/381,445

(22) Filed: May 3, 2006

(65) Prior Publication Data
US 2007/0259054 A1    Nov. 8, 2007

(51) Int. Cl.
  A61K 33/14    (2006.01)
  A01N 59/08    (2006.01)
  A23L 1/30     (2006.01)
  A23K 1/175    (2006.01)
  C12C 11/00    (2006.01)
  C12G 3/08     (2006.01)
  A61K 31/70    (2006.01)
  A01N 43/04    (2006.01)
  A61K 31/715   (2006.01)

(52) U.S. Cl. .................. 424/679; 424/680; 426/14; 426/74; 514/23; 514/53

(58) Field of Classification Search .............. None
See application file for complete search history.

(56) References Cited

U.S. PATENT DOCUMENTS

| | | |
|---|---|---|
| 4,093,750 A | 6/1978 | Babayan |
| 4,312,856 A | 1/1982 | Korduner et al. |
| 4,435,440 A | 3/1984 | Hough et al. |
| 4,775,546 A | 10/1988 | Higurashi et al. |
| 4,839,347 A | 6/1989 | Franz |
| 4,927,646 A | 5/1990 | Jenner et al. |
| 5,017,389 A | 5/1991 | Green |
| 5,028,437 A | 7/1991 | Jerrett |
| 5,085,876 A | 2/1992 | Tsau |
| 5,106,632 A | 4/1992 | Wong et al. |
| 5,114,723 A | 5/1992 | Stray-Gundersen |
| 5,292,722 A | 3/1994 | Wilmore |
| 5,364,652 A | 11/1994 | Ohkuma et al. |
| 5,378,484 A | 1/1995 | Suwa et al. |
| 5,380,541 A | 1/1995 | Beyts et al. |
| 5,403,604 A | 4/1995 | Black, Jr. et al. |
| 5,417,994 A | 5/1995 | Chang et al. |
| 5,443,830 A | 8/1995 | Moore et al. |
| 5,464,619 A | 11/1995 | Kuznicki et al. |
| 5,478,582 A | 12/1995 | Smith et al. |
| 5,489,440 A | 2/1996 | Ndife et al. |
| 5,561,111 A | 10/1996 | Guerrant et al. |
| 5,631,038 A | 5/1997 | Kurtz et al. |
| 5,733,579 A | 3/1998 | Wolf et al. |
| 5,780,094 A | 7/1998 | King |
| 5,817,364 A | 10/1998 | Olin |
| 5,851,578 A | 12/1998 | Gandhi |
| 5,869,458 A | 2/1999 | Waite et al. |
| 5,869,459 A | 2/1999 | Waite et al. |
| 5,876,763 A | 3/1999 | Montner et al. |
| 5,882,706 A | 3/1999 | Kawashima |
| 5,891,888 A | 4/1999 | Strahl |
| 5,980,968 A | 11/1999 | Booth |
| 6,039,987 A | 3/2000 | Strahl |
| 6,126,981 A | 10/2000 | Lee et al. |
| 6,126,986 A | 10/2000 | Harris et al. |
| 6,156,332 A | 12/2000 | Bakal et al. |
| 6,159,942 A | 12/2000 | St. Cyr et al. |
| 6,159,943 A | 12/2000 | Butler et al. |
| 6,162,474 A | 12/2000 | Chen et al. |
| 6,235,322 B1 | 5/2001 | Lederman |
| 6,290,997 B1 | 9/2001 | Villagran et al. |
| 6,429,198 B1 | 8/2002 | St. Cyr et al. |
| 6,525,027 B2 | 2/2003 | Vazquez et al. |
| 6,534,480 B2 | 3/2003 | Cyr et al. |
| 6,555,149 B2 | 4/2003 | Fridlyand |
| 6,569,477 B2 | 5/2003 | Lederman |
| 6,572,898 B2 | 6/2003 | Nelson et al. |
| 6,582,722 B1 | 6/2003 | Clark et al. |
| 6,730,336 B2 | 5/2004 | Villagran et al. |
| 6,730,337 B2 | 5/2004 | Hutt et al. |
| 6,730,342 B2 | 5/2004 | Saito et al. |

(Continued)

FOREIGN PATENT DOCUMENTS

| | | |
|---|---|---|
| EP | 0 393 909 | 10/1990 |
| GB | 1 252 781 | 11/1971 |
| WO | WO 90/02494 | 3/1990 |
| WO | WO 94/06412 | 3/1994 |
| WO | WO 98/30113 | 7/1998 |
| WO | WO 03/024403 A2 | 3/2003 |
| WO | WO 03/088901 | * 10/2003 |

OTHER PUBLICATIONS

International Search Report and Written Opinion, dated Nov. 9, 2007 for Application Serial No. PCT/US2007/068108, 19 pages.
"Approximate pH of Foods and Food Products", US FDA/CFSAN, http://www.cfsan.fda.gov/~comm/lacf-phs.html, 14 pages, Oct. 2003 (Hypertext updated Mar. 24, 2004).
Brody, Tom, "Hypokalemia", 5 pages, http://www.healthatoz.com/healthatoz/Atoz/common/standard/transform.jsp?requestURI=/healthatoz/Atoz/ency/hypokalemia.jsp, printed Apr. 2006.
Cera Products nutritional information for CeraLyte, http://ceraproductsinc.com/research/..%5Cproductline%5Cnutrition.html, Cera Products, Inc., 1 page, printed date 2006.

(Continued)

*Primary Examiner*—Johann R Richter
*Assistant Examiner*—Tigabu Kassa
(74) *Attorney, Agent, or Firm*—Evan Law Group LLC

(57) ABSTRACT

An oral rehydration mixture (ORM) may include from 47 to 75 wt % of a glucose containing saccharide, from 6 to 13 wt % sodium chloride, from 6.5 to 19 wt % potassium chloride, from 2 to 5 wt % sodium citrate, from 10 to 16 wt % citric acid, and from 0.3 to 0.5 wt % of a chlorinated sucrose isomer. The ORM may be combined with water to provide an oral rehydration solution (ORS). A method of treating dehydration may include administering to a subject the ORS.

11 Claims, 1 Drawing Sheet

U.S. PATENT DOCUMENTS

| | | | |
|---|---|---|---|
| 6,742,552 | B2 | 6/2004 | Raniwala |
| 6,770,305 | B2 | 8/2004 | Nelson et al. |
| 6,855,358 | B1 | 2/2005 | Nickolas et al. |
| 6,866,873 | B2 | 3/2005 | Stern |
| 6,890,581 | B2 | 5/2005 | Vernon et al. |
| 6,906,038 | B2 | 6/2005 | Mazer |
| 6,921,549 | B2 | 7/2005 | Blank et al. |
| 7,026,298 | B2 | 4/2006 | Phillips et al. |
| 2002/0110621 | A1 | 8/2002 | Robergs et al. |
| 2003/0003212 | A1 | 1/2003 | Chien et al. |
| 2003/0077333 | A1 | 4/2003 | Phillips et al. |
| 2003/0134804 | A1 | 7/2003 | King et al. |
| 2003/0194448 | A1 | 10/2003 | Mitchell et al. |
| 2004/0058034 | A1 | 3/2004 | Mehansho et al. |
| 2004/0076687 | A1 | 4/2004 | Thompson |
| 2004/0213881 | A1 | 10/2004 | Chien et al. |
| 2005/0186320 | A1 | 8/2005 | Blank |
| 2005/0238779 | A1 | 10/2005 | Isoya et al. |

OTHER PUBLICATIONS

Oral Rehydration Therapy Fact Sheet, http://www.ceraproductsinc.com/research/documents/ORTCHARTandFormularySheet_2pages_032706.pdf, Cera Products, Inc., 2 pages, printed date 2006.

"Why CeraLyte ORS?", Cera Products, Inc., 3 pages, 1998.

"Commodity Specification Canned Juice", USDA FV305-CS1, 30 pages, Apr. 2004.

Elliot, "The role of human perfusion techniques in the assessment of oral rehydration solutions," *Acta Paediatr Scand Suppl*, 364, 31-39, 1989.

Enfamil Enfalyte product information, http://www.meadjohnson.com/professional/products/enfalyte.html, 3 pages, 2004.

ESPGAN Working Group, "Recommendations for Composition of Oral Rehydration Solutions for the Children of Europe—Report of an ESPGAN Working Group" *J. Pediatr. Gastroenterol. Nutr.*, 14:113-115, 1992.

Farthing, "Disease-related animal models for optimizing oral rehydration solution composition," *Acta Paediatr Scand Suppl*, 364, 23-30, 1989.

Gatorade Beverage Comparison Chart, http://gssiweb-de.com/pdf/gatorade_bev_chart.pdf#search=%22gatorade%20beverage%20comparison%20chart%22, 2 pages, labeled as A, printed Oct. 2005.

Gatorade Beverage Comparison Chart, http://www.gssiweb.com/pdf/gatorade_bev_chart.pdf#search=%22gatorade%20beverage%20comparison%20chart%22, 2 pages, labeled as B, printed Sep. 2005.

Gerber Liquilytes Oral Electrolyte Maintenance Solution Instant Mix, Fruit Punch, http://www.walgreens.com/store/product.jsp?CATID=100819&navAction=jump&navCount=0&id=prod1323377, 3 pages, printed date Dec. 2006.

Hunt et al., "Water and solute absorption from a new hypotonic oral rehydration solution: evaluation in human and animal perfusion models," *Gut*, 33:1652-1659, 1992.

Kelly, D.G. et al., "Oral Rehydration Solution: A "Low-Tech" Oft Neglected Therapy," *Pract. Gastroenterol.*, 28:51-62, 2004.

"Managing Acute Gastroenteritis Among Children", *Morbidity and Mortality Weekly Report—Recommendations and Reports*, John M. Ward, ed., vol. 52, RR-16, 20 pages, 2003.

Matthews, "Frozen Concentrated Orange Juice From Florida Oranges", Fact Sheet FS8, Institute of Food and Agricultural Sciences, University of Florida, 4 pages, Apr. 1994.

"Multicentre evaluation of reduced-osmolarity oral rehydration salts solution," *The Lancet*, 345, pp. 282-285, 1995.

Nalin et al., "Clinical Concerns About Reduced-Osmolarity Oral Rehydration Solution", *JAMA*, vol. 291, No. 21, 2632-2635, Jun. 2, 2004.

Oral Rehydration Salts product information, Jianis Brothers, http://rehydrate.org/resources/jianas.htm, 1 page, Jan. 2006.

Oralsuero technical report, Laboratorios Casen Fleet, http://www.casenfleet.com/en/ficha_oralsuero.htm, 2 pages, 2002.

"Oral Rehydration Solutions: Packaged", Rehydration Project, http://rehydrate.org/solutions/packaged.htm, 6 pages, Jul. 2006.

"New Formula for Rehydration Salts—Studies", Rehydration Project, http://www.rehydrate.org/ors/newformula_studies.htm, 2 pages, Apr. 2006.

Pedialyte®, Online Product Handbook, http://rpdcon40.ross.com/pn/PediatricProducts.NSF/web_Ross.com_XML_PediatricNutrition/CCF3870065DFF53585256A80007546E8?OpenDocument, 3 pages, printed Jun. 12, 2006.

Pedialyte® product information, http://rpdcon40.ross.com/pn/PediatricProducts.NSF/0/ccf3870065dff53585256a80007546e8?OpenDocument&ExpandSection=5, 5 pages, printed Jun. 12, 2006.

Pignatelli et al., "Comparison of Three Oral Rehydration Strategies in the Treatment of Acute Diarrhea in a Tropical Country", *Current Therapeutic Research*, vol. 64, No. 3, 189-202, Mar. 2003.

"Reduced Osmolarity Oral Rehydration Salts (ORS) Formulation", UNICEF and WHO, available at http://www.who.int/child-adolescent-health/New_Publications/NEWS/Expert_consultation.htm, 14 pages, Jul. 18, 2001.

Rehydralyte®, Online Product Handbook, http://rpdcon40.ross.com/pn/PediatricProducts.NSF/web_Ross.com_XML_PediatricNutrition/96A5745B1183947385256A80007546E5?OpenDocument, 3 pages, printed Jun. 12, 2006.

Sandhu et al., "Optmising oral rehydration solution composition in model systems: studies in normal mammalian small intestine", *Acta Paediatr Scand Suppl*. 364, 17-22, 1989.

Sentongo, "The Use of Oral Rehydration Solutions in Children and Adults", *Current Gastroenterology Reports* 6:307-313, 2004.

"Situation and Outlook for Orange Juice," USDA, 7 pages, Jan. 2004.

"Situation and Outlook for Orange Juice," USDA, 3 pages, Apr. 2005.

"Situation and Outlook for Orange Juice," USDA, 3 pages, Feb. 2006.

Sueroral Casen product information, Laboratorios Casen Fleet, http://www.casenfleet.com/en/prospecto_sueroral.htm, 4 pages, 2002.

Sueroral Casen technical data sheet, Laboratorios Casen Fleet, http://www.casenfleet.com/en/ficha_sueroral.htm, 4 pages, 2002.

Sueroral Hiposodico product information, Laboratorios Casen Fleet, http://www.casenfleet.com/en/prospecto_sueroral_hiposodico.htm, 3 pages, 2002.

Sueroral Hiposodico technical data sheet, Laboratorios Casen Fleet, http://www.casenfleet.com/en/ficha_sueroral_hiposodico.htm, 3 pages, 2002.

\* cited by examiner

ORAL REHYDRATION COMPOSITIONS

BACKGROUND

Fruit juices historically have been popular beverages for adult consumption. In addition to their palatability, fruit juices are considered to have nutritional value due to their content of vitamins, minerals, antioxidants and other components. One drawback to fruit juices, however, is their high content of sugar and calories. For example, despite its high sugar content, orange juice typically has been considered one of the most beneficial fruit juices and has been popular for its taste and texture. However, orange juice consumption has been declining in the United States by about 4% annually since 2004, due to a popular trend of reduced carbohydrate diets. The high sugar content of fruit juices also has caused health professionals to discourage their use in the maintenance of hydration or in oral rehydration therapy.

Oral rehydration therapy (ORT) involves the administration of an oral rehydration solution (ORS) containing glucose and sodium in water. It is estimated that over one million lives are saved each year due to the use of ORT, primarily in developing countries. An ORS provides rapid, effective hydration because sodium ion absorption in the intestines causes water molecules associated with the sodium ion to be absorbed as well. This sodium absorption is activated by glucose. Thus, water can be absorbed more rapidly from an ORS containing both sodium and glucose than from water alone. An ORS can be used to treat acute infectious diarrhea and/or vomiting, to treat hyponatremia or hypohydration due to exercise or changes in altitude, and to maintain a healthy level of hydration.

An ORS is an aqueous liquid containing from 35 to 90 milliequivalents per Liter (meq/L) of sodium ($Na^+$) and from 1.2 to 3.0 weight percent (wt %) of a glucose containing saccharide, and having a total osmolarity of from 200 to 311 meq/L. The glucose containing saccharide may be glucose (i.e. dextrose), or a saccharide that can be hydrolyzed to form a composition containing glucose. An ORS may also include potassium, chloride, and citrate and/or bicarbonate.

The World Health Organization (WHO) and United Nations Children's Fund (UNICEF) have recommended two ORS formulas. The initial formula has a glucose concentration of 111 meq/L, a sodium concentration of 90 meq/L, and a total osmolarity of 311 meq/L. The most recent formula has a glucose concentration of 75 meq/L, a sodium concentration of 75 meq/L, and a total osmolarity of 245 meq/L. Since the osmolarity of normal blood plasma is 275 to 295 meq/L, the latter formula is referred to as "hypoosmolar."

In addition, the European Society for Paediatric Gastroenterology, Hepatology and Nutrition (ESPGHAN) has recommended a hypoosmolar ORS formula for European children that has a glucose concentration of from 74 to 111 meq/L, a sodium concentration of 60 meq/L, and a total osmolarity of from 200 to 250 meq/L. One version of the ESPGHAN formula has a glucose concentration of 89 meq/L, a sodium concentration of 60 meq/L, and a total osmolarity of 240 meq/L. The WHO and ESPGHAN formulas are listed in Table 1.

TABLE 1

ORS Formulations Recommended by Health Professionals

| | Grams per 1 Liter ORS | | |
|---|---|---|---|
| | WHO[a] | WHO Hypoosmolar[a,b] | ESPGHAN[a,c] |
| Glucose, anhydrous | 20.0 | 13.5 | 16.0 |
| NaCl | 3.5 | 2.6 | 1.0 |
| KCl | 1.5 | 1.5 | 1.5 |
| Sodium citrate, dihydrate | 2.9 | 2.9 | 2.9 |
| Osmolarity (meq/L) | 311 | 245 | 240 |

[a]"Managing Acute Gastroenteritis Among Children", Morbidity and Mortality Weekly Report - Recommendations and Reports, John M. Ward, ed., vol. 52, RR-16, cover and p. 12.
[b]http://rehydrate.org/solutions/packaged.htm
[c]"Recommendations for Composition of Oral Rehydration Solutions for the Children of Europe - Report of an ESPGAN Working Group" J. Pediatr. Gastroenterol. Nutr., 14: 113-115, 1992.

A number of beverages are available in the United States that are marketed as providing hydration. These beverages include Pedialyte®, Rehydralyte®, and EqualLyte® (Abbott Laboratories; Abbott Park, Ill.); Enfalyte® (Mead Johnson & Company; Evansville, Ind.); CeraLyte® (Cera Products, Inc., Columbia, Md.); and Liquilytes® (Gerber Products Company; Parsippany, N.J.). The available formulas for these products are listed in Table 2.

TABLE 2

| | ORS Formulations[a,d,e] | | | | | |
|---|---|---|---|---|---|---|
| | Carbohydrate (grams/L) | Sodium (meq/L) | Potassium (meq/L) | Chloride (meq/L) | Citrate (meq/L) | Osmolarity (meq/L) |
| Pedialyte ® | 25* | 45 | 20 | 35 | 30 | 269 |
| Rehydralyte ® | 25 | 75 | 20 | 65 | 30 | 305 |
| EquaLyte ® | 25 | 78.2 | 22.3 | 67.6 | 30.1 | 337 |
| Enfalyte ® | 30** | 50 | 25 | 45 | 34 | 170-200 |
| CeraLyte ® | 40** | 50-90 | 20 | — | 30 | 220-260 |
| Liquilytes ® | 25 | 45 | 20 | 35 | 30 | 250 |

[d]Sentongo, T. A., "The Use of Oral Rehydration Solutions in Children and Adults," Current Gastroenterology Reports, 6: 307-313, 2004.
[e]Kelly, D. G. et al., "Oral Rehydration Solution: A "Low-Tech" Oft Neglected Therapy," Pract. Gastroenterol., 28: 51-62, 2004.
*Includes 5 grams fructose.
**Rice-based carbohydrates Despite their effectiveness in maintaining and restoring hydration, the typical lack of palatability of ORS's can result in an undesirably low level of acceptance by patients and consumers. The high sodium content in particular results in an undesirable salty taste. Attempts to cover this salty taste typically have produced an ORS having a taste that is too sweet for many adult palates. It would be desirable to provide an ORS having an improved adult palatability. It would also be desirable to provide an ORS that could provide at least some of the health benefits of a fruit juice while still providing an effective hydration benefit.

SUMMARY

In one aspect, the invention provides an oral rehydration mixture, including from 47 to 75 wt % of a glucose containing saccharide, from 6 to 13 wt % sodium chloride, from 6.5 to 19 wt % potassium chloride, from 2 to 5 wt % sodium citrate, from 10 to 16 wt % citric acid, and from 0.3 to 0.5 wt % of a chlorinated sucrose isomer.

In another aspect, the invention provides an oral rehydration solution, including water, from 1.2 to 1.8 wt % of a glucose containing saccharide, from 35 to 50 meq/L sodium, from 15 to 56 meq/L potassium, from 35 to 90 meq/L chloride, from 10 to 30 meq/L citrate, and from 0.01 to 0.5 g/L of a sweetener. The solution has an osmolarity from 200 to 311 meq/L.

In yet another aspect, the invention provides an oral rehydration solution, including water, from 1.2 to 3.0 wt % of a glucose containing saccharide, from 35 to 90 meq/L sodium, from 30 to 56 meq/L potassium, from 35 to 90 meq/L chloride, and from 10 to 30 meq/L citrate. The solution has an osmolarity from 200 to 311 meq/L.

In yet another aspect, the invention provides an oral rehydration solution, including water, from 1.2 to 3.0 wt % of a glucose containing saccharide, from 35 to 55 meq/L sodium, from 15 to 56 meq/L potassium, from 35 to 90 meq/L chloride, and from 10 to 25 meq/L citrate. The solution has an osmolarity from 200 to 270 meq/L.

In yet another aspect, the invention provides an oral rehydration solution, including water, from 1.3 to 1.9 wt % of a glucose containing saccharide, from 36 to 54 meq/L sodium, from 24 to 56 meq/L potassium, from 52 to 79 meq/L chloride, from 16 to 25 meq/L citrate, and from 0.08 to 0.12 g/L of a chlorinated sucrose isomer. The solution has an osmolarity from 200 to 311 meq/L.

In yet another aspect, the invention provides a method of making an oral rehydration solution, including combining water and an oral rehydration mixture.

In yet another aspect, the invention provides a method of treating dehydration, including administering to a subject an oral rehydration solution that includes water and an oral rehydration mixture.

In yet another aspect, the invention provides a method of treating dehydration, including administering to a subject an oral rehydration solution. The amount of oral rehydration solution administered may be from 0.35 to 5 Liters.

In yet another aspect, the invention provides a method of maintaining hydration, including administering to a subject an oral rehydration solution. The amount of oral rehydration solution administered may be from 0.35 to 5 Liters.

The following definitions are included to provide a clear and consistent understanding of the specification and claims.

The term "oral rehydration solution" (ORS) means an aqueous liquid including from 35 to 90 milliequivalents per Liter (meq/L) sodium and from 1.2 to 3.0 weight percent (wt %) of a glucose containing saccharide, and having a total osmolarity of from 200 to 311 meq/L. The liquid may be a fully dissolved solution, or it may include suspended or precipitated substances.

The term "oral rehydration mixture" means a composition including a glucose containing saccharide and sodium that, when combined with water, will form an ORS.

The term "glucose containing saccharide" means either glucose, or a saccharide that can be hydrolyzed to form a composition containing glucose. Reference to any saccharide by a single name also includes all forms of that saccharide which may be in equilibrium with the specific saccharide named, in aqueous mixture at room temperature. For example, the term "glucose" includes glucose and all 5- and 6-membered cyclic hemiacetals in equilibrium with glucose in aqueous mixture at room temperature.

The term "osmolarity" means the concentration of solute in a liquid, and is expressed in units of milliequivalents per Liter (meq/L). One milliequivalent is equal to one millimole of a solute in a liquid.

BRIEF DESCRIPTION OF THE DRAWINGS

The invention can be better understood with reference to the following drawings and description.

DETAILED DESCRIPTION

Figure 1:
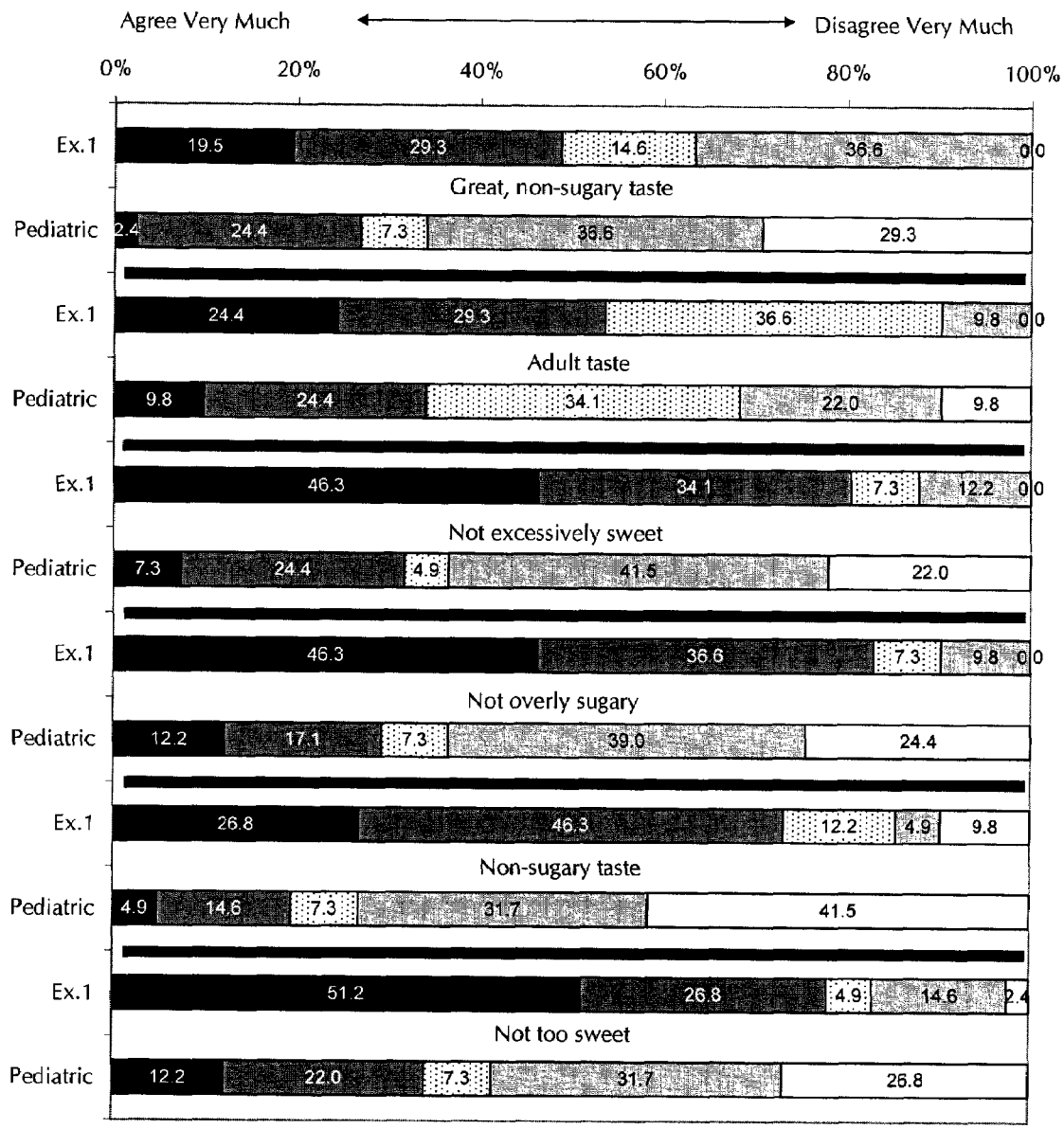
FIG. 1 is a graph of taste evaluation results.

The present invention makes use of the discovery that the palatability and/or nutritional properties of an oral rehydration solution (ORS) can be improved by the addition of a sweetener, by an increase in potassium content, and/or by an increase in the citric acid content. Such an ORS can have a taste that is neither salty nor too sweet, and that is acceptable to a large segment of the adult population. In some aspects, the ORS may have a taste and/or nutritional benefit similar to orange juice. A more acceptable flavor can increase an individual's willingness to consume an ORS, providing for more rapid recovery from dehydration or for the maintenance of a healthy level of hydration.

An ORS may contain an added sweetener. Preferably a sweetened ORS includes water, a sweetener, from 1.2 to 3.0 weight percent (wt %) of a glucose containing saccharide, from 35 to 90 meq/L sodium, from 15 to 56 meq/L potassium, from 35 to 90 meq/L chloride and from 10 to 30 meq/L citrate, and has an osmolarity from 200 to 311 meq/L. If the glucose containing saccharide is glucose, the 1.2 to 3.0 wt % range corresponds to 67 to 167 meq/L. The concentration of sweetener in the ORS may be from 0.01 to 0.5 grams per Liter (g/L). Examples of sweeteners include sodium saccharine, aspartame, acesulfame-K and chlorinated sucrose. Preferably the sweetener is chlorinated sucrose.

Chlorinated sucrose is a no-calorie sweetener made by replacing three of the hydroxy groups (OH) of the sugar molecule with chlorine (Cl). The chlorine atoms are tightly bound to the sugar molecule, thus making it exceptionally stable. This stability is believed to prevent the body from digesting the molecule, allowing the chlorinated sugar molecules to pass through the body unchanged. The chlorination process may create multiple isomers of the sugar, depending on the reaction conditions and other variables. Sucralose is the common name for one of the isomers resulting from the chlorination process. Sucralose is considered to be about 600 times sweeter than sugar and to have a medium intensity of sweetness coupled with a relatively long-lasting sweetness in the mouth.

The presence of a sweetener in the formulation may allow for a decrease in the amount of glucose containing saccharide in the ORS. Preferably a sweetened ORS contains a decreased level of glucose containing saccharide, of from 1.2 to 1.8 wt % (67 to 100 meq/L for glucose). Preferably a sweetened ORS contains a decreased level of sodium, of from 35 to 80 meq/L, and preferably of from 35 to 50 meq/L. Preferably a sweetened ORS is hypoosmolar, having an osmolarity from 200 to 270 meq/L. Preferably a sweetened ORS contains an elevated level of potassium, of from 30 to 56 meq/L. Preferably a sweetened ORS contains a decreased level of citrate, of from 10 to 25 meq/L citrate.

An ORS having a decreased amount of glucose containing saccharide may provide nutritional benefits, as well as improved patient or consumer acceptance. A decrease in glucose containing saccharide content can provide an ORS having fewer calories. A decrease in calories may be beneficial to individuals who monitor their caloric intake, especially to those who are on reduced calorie diets. A decrease in glucose containing saccharide content can also provide an ORS having a more adult taste. Many adults prefer beverages that are less sweet than beverages containing over 1.8 wt % glucose containing saccharide. Edible products marketed for children, including pediatric ORS's, typically include fructose instead of or in addition to a glucose containing saccharide, as this can provide an increased level of sweetness that is preferred by children. Thus, many adults associate sweet beverages with a pediatric, non-adult taste.

An ORS may contain an elevated level of potassium. Preferably a high-potassium ORS includes water, from 1.2 to 3.0 wt % of a glucose containing saccharide, from 35 to 90 meq/L sodium, from 30 to 56 meq/L potassium, from 35 to 90 meq/L chloride and from 10 to 30 meq/L citrate, and has an osmolarity from 200 to 311 meq/L. If the glucose containing saccharide is glucose, the 1.2 to 3.0 wt % concentration range corresponds to 67 to 167 meq/L.

Preferably a high-potassium ORS is hypoosmolar, having an osmolarity from 200 to 270 meq/L. Preferably a high-potassium ORS contains a decreased level of glucose containing saccharide, of from 1.2 to 1.8 wt % (67 to 100 meq/L for glucose). Preferably a high-potassium ORS contains a decreased level of sodium, of from 35 to 80 meq/L. Preferably a high-potassium ORS contains a decreased level of citrate, of from 10 to 25 meq/L citrate. A high-potassium ORS also may include a sweetener.

The presence of higher levels of potassium in an ORS may provide nutritional benefits in addition to the hydration benefit. For example, potassium deficiency (hypokalemia), which may be caused by diarrhea and vomiting, may result in cardiovascular irregularities or muscular cramping. Although typical ORS formulations include only 20 to 25 meq/L potassium, many fruit juices include from 30 meq/L potassium (apple juice) to 46 meq/L potassium (orange juice). The presence of potassium in an ORS at a concentration higher than 25 meq/L may contribute to the alleviation of hypokalemia and/or its symptoms. The presence of potassium in an ORS at a concentration higher than 25 meq/L may provide a taste and/or nutritional benefit similar to fruit juices.

An ORS may be hypoosmolar and may contain decreased levels of sodium and of citrate. Preferably a hypoosmolar ORS includes water, from 1.2 to 3.0 wt % of a glucose containing saccharide, from 35 to 55 meq/L sodium, from 15 to 56 meq/L potassium, from 35 to 90 meq/L chloride, and from 10 to 25 meq/L citrate, and has an osmolarity of from 200 to 270 meq/L. If the glucose containing saccharide is glucose, the 1.2 to 3.0 wt % range corresponds to 67 to 167 meq/L. A hypoosmolar ORS may include from 35 to 50 meq/L sodium, or from 40 to 50 meq/L sodium. Preferably a hypoosmolar ORS contains a decreased level of glucose containing saccharide, of from 1.2 to 1.8 wt % (67 to 100 meq/L for glucose). Preferably a hypoosmolar ORS contains an elevated level of potassium, of from 30 to 56 meq/L. A hypoosmolar ORS also may include a sweetener. Preferably a hypoosmolar ORS has an osmolarity from 200 to 270 meq/L, from 210 to 268 meq/L, from 220 to 260 meq/L, or from 225 to 255 meq/L.

A hypoosmolar ORS may provide benefits in the treatment of dehydration or in hydration maintenance. One possible benefit is a reduced risk of hypernatremia. Another possible benefit is a reduction in stool output when treating diarrhea, leading to a shortened duration of the diarrhea symptoms.

An ORS containing a concentration of sodium of less than 70 meq/L may provide benefits in the treatment of dehydration or in hydration maintenance. An ORS having a lower sodium concentration may provide more formulation options in preparing a hypoosmolar beverage. An ORS having a lower sodium concentration may also be more palatable than a similar ORS having a higher sodium concentration. Improvements in palatability may result in increased consumer acceptance or patient compliance in consuming an ORS.

In one example, an ORS may include water, from 1.3 to 1.9 wt % of a glucose containing saccharide, from 36 to 54 meq/L sodium, from 24 to 56 meq/L potassium, from 52 to 79 meq/L chloride, from 16 to 25 meq/L citrate, and from 0.08 to 0.12 g/L of a chlorinated sucrose isomer. Such an ORS may have an osmolarity from 200 to 311 meq/L. If the glucose containing saccharide is glucose, the 1.3 to 1.9 wt % range corresponds to 70 to 107 meq/L.

In another example, an ORS may include water, from 1.4 to 1.8 wt % of a glucose containing saccharide, from 40 to 50 meq/L sodium, from 27 to 51 meq/L potassium, from 59 to 72 meq/L chloride, from 18 to 22 meq/L citrate, and from 0.09 to 0.11 g/L of chlorinated sucrose isomer. Such an ORS may have an osmolarity from 225 to 293 meq/L. If the glucose containing saccharide is glucose, the 1.4 to 1.8 wt % range corresponds to 80 to 100 meq/L. Preferably the ORS is hypoosmolar, having an osmolarity from 225 to 270 meq/L.

An ORS may be prepared by combining the non-aqueous (i.e. "dry") ingredients with water to provide a liquid having the appropriate concentrations of ingredients. The dry ingredients may be combined with the water simultaneously, or one or more of the dry ingredients may be added separately. It may be desirable to provide all the dry ORS ingredients in a single composition, referred to as an oral rehydration mixture (ORM).

An ORM may include from 47 to 75 wt % of a glucose containing saccharide, from 6 to 13 wt % sodium chloride, from 6.5 to 19 wt % potassium chloride, from 2 to 5 wt % sodium citrate, from 10 to 16 wt % citric acid, and from 0.3 to 0.5 wt % of a chlorinated sucrose isomer. This ORM may be combined with water to provide an ORS including from 1.3 to 1.9 wt % glucose containing saccharide, from 36 to 54 meq/L sodium, from 24 to 56 meq/L potassium, from 52 to 79 meq/L chloride, from 16 to 25 meq/L citrate and from 0.08 to 0.12 g/L chlorinated sucrose isomer, and having an osmolarity of from 200 to 311 meq/L. If the glucose containing saccharide is glucose, the 1.3 to 1.90 wt % range corresponds to 70 to 107 meq/L.

An ORM may include from 53 to 71 wt % of a glucose containing saccharide, from 7 to 12 wt % sodium chloride, from 7.5 to 17 wt % potassium chloride, from 2.5 to 4 wt % sodium citrate, from 11 to 15 wt % citric acid, and from 0.35 to 0.45 wt % of a chlorinated sucrose isomer. This ORM may be combined with water to provide an ORS including from 1.4 to 1.8 wt % glucose containing saccharide, from 40 to 50 meq/L sodium, from 27 to 51 meq/L potassium, from 59 to 72 meq/L chloride, from 18 to 22 meq/L citrate and from 0.09 to 0.11 g/L chlorinated sucrose isomer, and having an osmolarity of from 225 to 293 meq/L. If the glucose containing saccharide is glucose, the 1.4 to 1.8 wt % range corresponds to 80 to 100 meq/L.

An ORM may include from 59 to 63 wt % of a glucose containing saccharide, from 7.5 to 8.5 wt % sodium chloride, from 8.5 to 13 wt % potassium chloride, from 2.8 to 3.2 wt % sodium citrate, from 12 to 13 wt % citric acid, and from 0.37 to 0.40 wt % of a chlorinated sucrose isomer. This ORM may be combined with water to provide an ORS including about 1.60 wt % glucose containing saccharide, about 45 meq/L sodium, from 30 to 46 meq/L potassium, about 66 meq/L chloride, about 20 meq/L citrate and about 0.1 g/L chlorinated sucrose isomer, and having an osmolarity of from 250 to 266 meq/L. If the glucose containing saccharide is glucose, the 1.60 wt % corresponds to 89 meq/L.

The glucose containing saccharide in an ORS or an ORM may be glucose, or may be a saccharide that can be hydrolyzed to form a composition containing glucose. Saccharides are polyhydroxy aldehydes or ketones, and include monosaccharides, disaccharides, oligosaccharides, and polysaccharides. Saccharides typically have a water solubility of at least one gram per Liter. Examples of glucose containing saccharides include glucose, sucrose, lactose, maltose, amylose, glycogen and maltodextrin. A variety of glucose containing saccharides may be present in an ORS or an ORM, as may other saccharides that do not contain glucose. Examples of saccharides that do not contain glucose include fructose, galactose, allose, altrose, mannose, gulose, idose, talose, ribose, arabinose, lyxose, ribose, xylose, erythrose, and threose.

The sodium in an ORM may be present as a cation of a salt. Examples of sodium salts include sodium chloride, sodium phosphate, sodium citrate, sodium carbonate, sodium bicarbonate, sodium hydroxide, and mixtures of these. The sodium in an ORS may be present as an ion in the liquid, and may be in equilibrium with a salt.

The potassium in an ORM may be present as a cation of a salt. Examples of potassium salts include potassium chloride, potassium phosphate, potassium citrate, potassium carbonate, potassium bicarbonate, potassium hydroxide, and mixtures of these. The potassium in an ORS may be present as an ion in the liquid, and may be in equilibrium with a salt.

The chloride in an ORM may be present as an anion of a salt. Examples of chloride salts include sodium chloride, potassium chloride, calcium chloride, magnesium chloride, and mixtures of these. The chloride in an ORS may be present as an ion in the liquid, and may be in equilibrium with a salt.

The citrate in an ORM may be present as citric acid, as a citric ester that can be hydrolyzed into citric acid or citrate ion, or as a citrate salt. Examples of citrate salts include sodium citrate, potassium citrate and mixtures of these. The citrate in an ORS may be present as the free acid or as an ion in the liquid, and may be in equilibrium with a salt. Some or all of the citrate may be replaced with a base, such as bicarbonate. Citrate can be metabolized to bicarbonate, and some ORS and ORM products list bicarbonate and/or citrate as a source of base in the formulations.

ORM formulations typically contain little or no citric acid, the citrate content instead being provided by sodium citrate and/or potassium citrate. An ORM containing increased levels of citric acid may provide taste benefits to an ORS prepared from the ORM. Orange juice typically contains about 25 to 45 meq/L citric acid, and has a pH from 3.3 to 4.2. In one example, an ORM containing from 12 to 13 wt % citric acid may be mixed with water to provide an ORS including approximately 20 meq/L citric acid and having a pH of about 3.3. Thus, the characteristic acidity of orange juice may be reproduced in an ORS, and may produce a taste that is similar to the desirable taste of orange juice. An ORS may have a reduced level of citrate (i.e. from 10 to 25 meq/L) even though it is prepared from an ORM having an increased level of citric acid, since an ORS can contain citrate in the form of sodium and/or potassium citrate salts.

An ORS or ORM may include one or more additional ingredients. Examples of additional ingredients in an ORS or ORM include flavorants, colorants, preservatives, excipients, gelling agents, indigestible oligosaccharides, rice derivatives, amino acids, zinc, calcium, vitamins, and dietary supplements. Preferably the amount of any additional ingredients in an ORS is such that the primary ingredients and the overall osmolarity remain within the desired ranges.

A flavorant may be present to add or modify a flavor in the ORS. Examples of flavorants include anise oil, cinnamon oil, vanilla, vanillin, cocoa, chocolate, menthol, grape, peppermint oil, oil of wintergreen, clove oil, bay oil, anise oil, eucalyptus, thyme oil, cedar leaf oil, oil of nutmeg, oil of sage, oil of bitter almonds, cassia oil, citrus oils such as lemon, orange, lime and grapefruit oils, and fruit essences, including apple, pear, peach, berry, wildberry, date, blueberry, kiwi, strawberry, raspberry, cherry, plum, pineapple, and apricot.

A colorant may be present to add or modify a color in the ORS. Examples of colorants include FD&C Red No. 3, FD&C Red No. 20, FD&C Yellow No. 6, FD&C Blue No. 2, D&C Green No. 5, FD&C Orange No. 5, D&C Red No. 8, caramel, ferric oxide, pigments, dyes, tints, titanium dioxide, grape skin extract, beet red powder, beta carotene, annato, carmine, turmeric, and paprika.

A preservative may be present to provide a longer shelf life to a pre-packaged ORS or ORM, or to extend the potability lifetime of an ORS. Examples of preservatives include potassium sorbate and sodium benzoate.

An excipient may be present to provide stability and/or flowability to the ingredients in an ORM and/or to modify or stabilize the viscosity of an ORS. Examples of excipients include silica, cellulose, cellulose esters, polyethylene glycol, and lecithin. Examples of excipients affecting viscosity may also include the gelling agents listed below, when present in low concentrations.

A gelling agent may be present in an ORM, such that an ORS prepared from the ORM can be formed into a gel, such as a flowable gel or a self-supporting gel. It has been reported that ORS gels may provide improved patient compliance in consuming an ORS. Examples of gelling agents include agar, alginic acid and salts, gum arabic, gum acacia, gum talha, cellulose derivatives, curdlan, fermentation gums, furcellaran, gelatin, gellan gum, gum ghatti, guar gum, iota carrageenan, irish moss, kappa carrageenan, konjac flour, gum karaya, lambda carrageenan, larch gum/arabinogalactan, locust bean gum, pectin, tamarind seed gum, tara gum, gum tragacanth, native and modified starch, xanthan gum and mixtures of these. An ORS gel is disclosed, for example, in U.S. Pat. No. 6,572,898 to Nelson et al.

An indigestible oligosaccharide may be present in an ORS or ORM. It has been reported that indigestible oligosaccharides may provide a benefit to the gastrointestinal tract. One possible explanation for a benefit is that indigestible oligosaccharides may help to suppress the growth of pathogenic organisms such as *Clostridium difficile*, and/or to selectively promote the growth of a nonpathogenic microbial flora. Examples of indigestible oligosaccharides include fructoologosaccharides, inulins such as raftilose, and xylooligosaccharides. If present, an indigestible oligosaccharide may have a concentration in an ORS of from 1 to 100 g/L, or from 3 to 30 g/L. An ORS containing an indigestible oligosaccharide is disclosed, for example, in U.S. Pat. No. 5,733,759 to Wolf et al.

Substances derived from rice may be present in an ORS or ORM. It has been reported that various components of rice may provide a benefit in the treatment of diarrhea and/or dehydration. Examples of rice derivatives include rice flour, which may provide a source of carbohydrate in addition to the glucose containing saccharide. A rice supplemented ORS is disclosed, for example, in U.S. Pat. No. 5,489,440 to Ndife et al and in U.S. Patent Application Publication No. 2003/0194448 A1 to Mitchell et al.

Amino acids may be present in an ORS or ORM, as individual amino acids or as peptides containing two or more amino acids linked together. It has been reported that glutamine may promote healing of the gut, and that arginine supplements may be helpful for patients having small bowel impairment. An ORS containing glutamine and/or a glutamine containing substance is described, for example, in U.S. Pat. No. 5,561,111, to Guerrant et al.

Zinc or a zinc containing substance may be present in an ORS or ORM. It has been reported that the presence of zinc in an ORS may help replace zinc that has been lost due to diarrhea and/or vomiting. It has also been reported that the presence of zinc in an ORS may help reduce the severity and/or duration of diarrhea. Examples of zinc containing substances include zinc gluconate, zinc sulfate, zinc chloride, zinc citrate, zinc bicarbonate, zinc carbonate, zinc hydroxide, zinc lactate, zinc acetate, zinc fluoride, zinc bromide, zinc sulfonate and mixtures of these. If present, the zinc may have a concentration in an ORS of from 0.3 to 95 meq/L, from 0.6 to 5 meq/L, from 0.6 to 3 meq/L, or from 0.6 to 1.2 meq/L. An ORS containing zinc is disclosed, for example, in U.S. Pat. No. 7,026,298 to Phillips et al.

Calcium or a calcium containing substance may be present in an ORS or ORM. An ORS containing calcium may be desirable, particularly for individuals who consume calcium supplements. Examples of calcium containing substances include calcium chloride, calcium oxide, calcium hydroxide, calcium carbonate, calcium orthophosphate (including mono-, di- and tricalcium phosphate), calcium lactate, calcium gluconate, calcium citrate, calcium acetate, calcium ascorbate, calcium tartarate, calcium malate and mixtures of these. If present, the calcium may be present from 5 to 30 meq/L, from 10 to 25 meq/L, or from 15 to 20 meq/L. A beverage containing calcium and asserted to provide hydration is disclosed, for example, in U.S. Pat. No. 6,730,337 to Hutt et al.

A vitamin may be present in an ORS or ORM. An ORS containing one or more vitamins may be desirable, particularly for individuals who consume vitamin supplements. Examples of vitamins that may be present include biotin, choline, folate, niacin, pantothenic acid, vitamin Bi (thiamin), vitamin B2 (riboflavin), vitamin A, vitamin $B_6$, vitamin $B_{12}$, vitamin C, vitamin D, vitamin E, and vitamin K. If present, a vitamin may have a concentration in an ORS sufficient to provide from 5% to 100% of the recommended daily value. In one example, an ORS including vitamin C may contain more than 100% of the recommended daily value, for example 200%, 300% or 500% of the recommended daily value vitamin C. In another example, an ORS may contain from 0.01 to 0.5 wt % vitamin C, from 0.05 to 0.2 wt % vitamin C, or about 0.1 wt % vitamin C. A beverage containing vitamin C and asserted to provide hydration is disclosed, for example, in U.S. Pat. No. 6,730,337 to Hutt et al.

A dietary supplement may be present in an ORS or ORM. An ORS containing one or more dietary supplements may be desirable, particularly for individuals who consume dietary supplements. Examples of dietary supplements that may be present include minerals, such as iron, phosphorus, iodine, magnesium, selenium, copper, manganese, chromium, molybdenum, nickel, tin, silicon, vanadium and boron; antioxidants, such as carotene, eugenol, lutein, lycopene, and flavonoids; glucosamine; glycosaminoglycans, such as chondroitin and hyaluronic acid; probiotics, such as *Lactobacillus reuteri* and *Lactobacillus acidophilus*; and herbal extracts. If present, a dietary supplement may have a concentration in an ORS sufficient to provide from 5% to 100% of the recommended daily value.

An ORM may be in the form of a solid, such as a powdered solid, a granulated solid, or one or more tablets. A powdered or granulated solid may also be contained in a capsule, such as a water soluble capsule. An ORM may be in the form of a viscous concentrate, such as a syrup. For example, an aqueous liquid may be prepared by combining water and the remaining ORS ingredients, and then water may be removed from the mixture to form a concentrate.

An ORM may be packaged in a container, such as a sachet, a packet, an envelope, a tube, an ampoule, a bottle, or a tub. The amount of ORM in an individual container may be sufficient to prepare a single serving of ORS when mixed with water. For example, the amount of ORM may provide 12 fluid ounces (fl.oz.) of ORS (0.35 L). In another example, the amount of ORM may provide 1 L of ORS. The amount of ORM in an individual package may be sufficient to prepare multiple servings of ORS. For example, the amount of ORM in a container may provide more than 1 L of ORS.

An ORS may be packaged in a container such as a glass or plastic bottle, a plastic pouch, or a paper-based carton. In one example, an ORS may be formed by combining water with the remaining ORS ingredients, agitating and/or heating the mixture to dissolve the ingredients, and then packaging the ORS in a container. The ORS may be sterilized before or after being packaged, such as by pasteurization, ultrapasteurization and/or irradiation. The ORS may be packaged in a container that includes an oxygen barrier, an oxygen scavenger, and/or an ultraviolet radiation barrier. A single package of ORS may contain a single serving, such as 12 fl.oz. (0.35 L) or 1 L. A single package of ORS may contain multiple servings, such as multiples of 12 fl.oz. (0.35 L) or of 1 L.

An ORS may be packaged in non-liquid forms. In one example, an ORS may be packaged as a gel containing one or more gelling agents as described above. In another example, an ORS may be packaged as a frozen composition. Frozen ORS may be in the form of ice cubes, ice on a stick (i.e. "freezer pop"), crushed ice, or shaved ice, for example. It has been reported that frozen ORS may provide improved patient compliance in consuming an ORS. Frozen ORS is disclosed, for example, in U.S. Pat. No. 5,869,459 to Waite et al.

A method of treating dehydration includes orally administering an ORS to a subject. Orally administering an ORS may include combining an ORM and water to form the ORS. The amount of ORS administered may be from 0.35 to 5 Liters. The effective amount of ORS may vary depending on the body mass of the subject and the degree of dehydration.

A method of maintaining hydration includes orally administering an ORS to a subject. Orally administering an ORS may include combining an ORM and water to form the ORS. The amount of ORS administered may be from 0.35 to 5

Liters. The effective amount of ORS may vary depending on the body mass of the subject and the existing level of hydration.

The following examples are provided to illustrate one or more preferred embodiments of the invention. Numerous variations may be made to the following examples that lie within the scope of the invention.

EXAMPLES

Example 1

Preparation of Oral Rehydration Mixture

The ingredients listed in Table 3 were combined to form a powder mixture. The amounts of each ingredient are listed for preparation of a one Liter aqueous mixture and for preparation of a 12 fluid-ounce (fl.oz.) aqueous mixture (0.35 L). The mixture was combined with water to provide an ORS. The ionic content of the ORS is listed in Table 4.

Example 2

Sweetness Taste Evaluation of ORS

The ORS of Example 1 was subjected to a taste test by 41 adult test subjects age 18 or older. The subjects were provided a 12 fl.oz. (0.35 L) sample of the ORS of Example 1 and a 12 fl.oz. (0.35 L) sample of a pediatric ORS (Pedialyte® oral electrolyte maintenance solution, fruit flavor; ABBOTT LABORATORIES, Abbott Park, Ill.). The ionic contents of the two solutions are listed in Table 4. The formula for the pediatric ORS was compiled from product information from the manufacturer, (http://rpdcon40.ross.com/pn/Pediatric-Products. NSF/web_Ross.com_XML_PediatricNutrition/ CCF3870065DFF53585256A80007546E8?OpenDocument) and from "Managing Acute Gastroenteritis Among Children", *Morbidity and Mortality Weekly Report-Recommendations and Reports*, John M. Ward, ed., vol. 52, RR-16, p. 12.

TABLE 3

Oral Rehydration Mixture

|  | Weight % | Grams/1 Liter ORS | Grams/12 fl. oz. ORS |
|---|---|---|---|
| Glucose* | 62.57 | 16.0 | 5.63 |
| NaCl* | 8.17 | 2.09 | 0.74 |
| KCl* | 8.76 | 2.24 | 0.79 |
| Sodium Citrate* | 3.09 | 0.79 | 0.28 |
| Citric Acid* | 12.91 | 3.30 | 1.16 |
| Sucralose | 0.39 | 0.10 | 0.04 |
| Artificial Flavor | 3.91 | 1.0 | 0.35 |
| FD&C Yellow dye #6 | 0.20 | 0.05 | 0.02 |
| Total | — | 25.57 | 9.00 |

*Granular, anhydrous

TABLE 4

Comparison Of Oral Rehydration Solutions

| | Amount per Liter | |
|---|---|---|
| | Example 1 ORS | Pediatric ORS |
| Glucose | 16 g (89 meq/L) | 20 g (111 meq/L) |
| Fructose | — | 5 g (28 meq/L) |
| Sodium | 45 meq | 45 meq |
| Potassium | 30 meq | 20 meq |
| Chloride | 66 meq | 35 meq |
| Citrate | 20 meq | 30 meq |
| Osmolarity | 250 meq/L | 269 meq/L |
| Calories | 64 cal | 100 cal |

Each test subject was asked to rate each sample with respect to five sweetness evaluation parameters. The subjects had to indicate whether each sample was much too sweet, somewhat too sweet, just right, not quite sweet enough, or not sweet enough at all. The results of this aspect of the taste evaluation are listed in Table 5.

TABLE 5

Sweetness Taste Evaluation

| | Percentage of Responses | |
|---|---|---|
| | Example 1 | Pediatric ORS |
| Much too sweet | 0 | 20 |
| Somewhat too sweet | 22 | 49 |
| Just right | 41 | 27 |
| Not quite sweet enough | 29 | 2 |
| Not sweet enough at all | 7 | 2 |

The data establishes that adult test subjects evaluated the Example 1 ORS as significantly less sweet than the pediatric ORS. Referring to Table 5, 41% of the subjects evaluated the Example 1 ORS as "just right", whereas only 27% agreed with this evaluation for the pediatric ORS. The pediatric ORS was rated somewhat too sweet or much too sweet by 69% of the adult subjects. In contrast, only 22% of the adult subjects rated the Example 1 ORS as somewhat too sweet, and none of the subjects rated the Example 1 ORS as much too sweet.

Example 3

Adult Taste Evaluation of ORS

The test subjects of Example 2 also were asked to rate the Example 1 ORS and the pediatric ORS with respect to six adult taste evaluation parameters. The subjects had to indicate whether they agreed very much, agreed somewhat, neither agreed nor disagreed, disagreed somewhat, or disagreed very much with the following descriptions for each sample:
a) Great, non-sugary taste
b) Has an adult taste
c) Not excessively sweet
d) Not overly sweet
e) Non-sugary taste
f) Not too sweet The results of this aspect of the taste evaluation are shown graphically in FIG. 1. The data establishes that adult test subjects evaluated the Example 1 ORS as having a taste profile more consistent with an adult taste preference, relative to the taste profile of the pediatric ORS. The Example 1 ORS was rated as having an "adult taste" by 53% of the adult subjects, whereas only 34% of the adult subjects agreed with this evaluation for the pediatric ORS. In the more objective taste parameters regarding sweetness and non-sugary taste, the Example 1 ORS was further distinguished from the pediatric ORS. The adult test subjects were almost twice as likely to rate the Example 1 ORS as having a "great, non-sugary taste" than they were for the pediatric ORS. The subjects were 2-3 times as likely to rate the Example 1 ORS as having a "not excessively sweet taste", as being "not excessively sweet", as being "not overly sugary", or as being "not too sweet" than they were for the pediatric ORS. The subjects were over 3 times as likely to rate the Example 1 ORS as having a "non-sugary taste" than they were for the pediatric ORS.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. An oral rehydration mixture, comprising:
   from 47 to 75 wt% of a glucose containing saccharide,
   from 6 to 13 wt% sodium chloride,
   from 6.5 to 19 wt% potassium chloride,
   from 2 to 5 wt% sodium citrate,
   from 10 to 16 wt% citric acid, and
   from 0.3 to 0.5 wt% of a chlorinated sucrose isomer.
2. The oral rehydration mixture of claim 1, comprising:
   from 53 to 71 wt% of glucose containing saccharide,
   from 7 to 12 wt% sodium chloride,
   from 7.5 to 17 wt% potassium chloride,
   from 2.5 to 4 wt% sodium citrate,
   from 11 to 15 wt% citric acid, and
   from 0.35 to 0.45 wt% of chlorinated sucrose isomer.
3. The oral rehydration mixture of claim 1, comprising:
   from 59 to 63 wt% of glucose containing saccharide,
   from 7.5 to 8.5 wt% sodium chloride,
   from 8.5 to 13 wt% potassium chloride,
   from 2.8 to 3.2 wt% sodium citrate,.
   from 12 to 13 wt% citric acid, and
   from 0.37 to 0.40 wt% of chlorinated sucrose isomer,
4. The oral rehydration mixture of claim 1, further comprising at least one ingredient selected from the group consisting of flavorants, colorants, preservatives, excipients, gelling agents, indigestible oligosaccharides, rice derivatives, amino acids, zinc, calcium, vitamins, and dietary supplements.
5. The oral rehydration mixture of claim 1, where the mixture is in the form of a solid.
6. The oral rehydration mixture of claim 5, where the mixture is packaged in a container.
7. The oral rehydration mixture of claim 6, where the container is selected from the group consisting of a sachet, a packet, and an envelope.
8. The oral rehydration mixture of claim 6, where the amount of mixture in the container is sufficient to prepare a single serving of oral rehydration solution having a volume of from 0.35 to 1 Liter.
9. The oral rehydration mixture of claim 6, where the amount of mixture in the container is sufficient to prepare more than 1 Liter of oral rehydration solution.
10. A method of making an oral rehydration solution, comprising:
    combining water and the oral rehydration mixture of claim 1.
11. A method of treating dehydration, comprising:
    administering to a subject an oral rehydration solution comprising water and the oral rehydration mixture of claim 1.

* * * * *